United States Patent
Yarden et al.

(10) Patent No.: US 9,599,521 B2
(45) Date of Patent: Mar. 21, 2017

(54) INTERFACE BETWEEN VITAL-SIGNS SENSORS AND PATIENT MONITOR

(71) Applicant: Medisim Ltd., Neve Ilan (IL)

(72) Inventors: Moshe Yarden, Mevaseret Zion (IL); Vladimir Gorovetz, MaAle Adumim (IL)

(73) Assignee: Medisim, LTD. (IL)

( * ) Notice: Subject to any disclaimer, the term of this patent is extended or adjusted under 35 U.S.C. 154(b) by 72 days.

(21) Appl. No.: 14/164,328

(22) Filed: Jan. 27, 2014

(65) Prior Publication Data
US 2015/0211944 A1 Jul. 30, 2015

(51) Int. Cl.
| | |
|---|---|
| A61B 5/05 | (2006.01) |
| G01K 15/00 | (2006.01) |
| A61B 5/00 | (2006.01) |
| A61B 5/021 | (2006.01) |
| A61B 5/026 | (2006.01) |
| A61B 5/145 | (2006.01) |
| G01K 7/16 | (2006.01) |
| A61B 5/024 | (2006.01) |
| G01K 1/02 | (2006.01) |
| G01K 7/25 | (2006.01) |
| G01K 13/00 | (2006.01) |

(52) U.S. Cl.
CPC ............ *G01K 15/005* (2013.01); *G01K 1/02* (2013.01); *G01K 7/25* (2013.01); *G01K 13/002* (2013.01); *A61B 5/024* (2013.01)

(58) Field of Classification Search
CPC ...... G01K 15/005; A61B 5/7278; A61B 5/01; A61B 5/024
USPC .................................................. 600/549, 374
See application file for complete search history.

(56) References Cited

U.S. PATENT DOCUMENTS

| | | | |
|---|---|---|---|
| 3,776,040 A | 12/1973 | Gould | |
| 3,921,621 A | 11/1975 | Baessler | |
| 4,407,292 A | 10/1983 | Edrich | |
| 4,467,633 A | 8/1984 | McEwen et al. | |
| 5,073,034 A | 12/1991 | Beran et al. | |
| 5,313,185 A | 5/1994 | DeChurch | |

(Continued)

OTHER PUBLICATIONS

U.S. Appl. No. 12/880,102 Office Action dated Apr. 29, 2013.
U.S. Appl. No. 12/880,102 Office Action dated Sep. 9, 2013.

*Primary Examiner* — Jeffrey G Hoekstra
*Assistant Examiner* — Nicholas E Kolderman
(74) *Attorney, Agent, or Firm* — Lerner, David, Littenberg, Krumholz & Mentlik, LLP

(57) ABSTRACT

An apparatus includes at least one sensor, a connector and a conversion unit. The sensor is coupled to a patient body so as to measure a physiological parameter of the body. The connector coupled to a patient monitor, which measures a value of the physiological parameter by applying a test signal via the connector and measuring a response signal on the connector in response to the test signal. The conversion unit is coupled between the at least one sensor and the connector, and is configured to determine a corrected value of the physiological parameter, to calculate an auxiliary signal that, in combination with the test signal produced by the patient monitor, causes the response signal on the connector to represent the corrected value of the physiological parameter, and to generate and output the auxiliary signal to the connector so as to cause the patient monitor to measure the corrected value.

20 Claims, 3 Drawing Sheets

(56) References Cited

U.S. PATENT DOCUMENTS

| | | |
|---|---|---|
| 5,655,305 A | 8/1997 | Fletcher |
| 5,857,777 A | 1/1999 | Schuh |
| 6,030,342 A | 2/2000 | Amano et al. |
| 6,086,247 A | 7/2000 | Von Hollen |
| D430,812 S | 9/2000 | Levin et al. |
| 6,179,786 B1 | 1/2001 | Young |
| 6,238,354 B1 | 5/2001 | Alvarez |
| 6,248,083 B1 | 6/2001 | Smith et al. |
| 6,270,463 B1 | 8/2001 | Morris et al. |
| 6,280,397 B1 | 8/2001 | Yarden et al. |
| 6,292,685 B1 | 9/2001 | Pompei |
| 6,735,379 B2 | 5/2004 | Salmon et al. |
| 6,921,198 B2 * | 7/2005 | Gruszecki ............ G01K 13/002 374/1 |
| 6,929,611 B2 | 8/2005 | Koch |
| 7,059,769 B1 | 6/2006 | Potega |
| 7,268,573 B2 * | 9/2007 | Jang ................ G01R 31/31924 324/762.01 |
| 7,479,116 B2 | 1/2009 | Yarden et al. |
| 7,484,887 B2 * | 2/2009 | Shidemantle ............ G01K 7/25 374/1 |
| 7,597,668 B2 | 10/2009 | Yarden |
| 7,625,117 B2 | 12/2009 | Haslett et al. |
| 7,641,390 B2 | 1/2010 | Shidemantle et al. |
| 8,185,341 B2 | 5/2012 | Yarden et al. |
| 8,328,420 B2 | 12/2012 | Abreu |
| 2003/0045781 A1 * | 3/2003 | Rosenheimer ....... A61B 5/0002 600/300 |
| 2004/0019293 A1 | 1/2004 | Schweitzer et al. |
| 2004/0252750 A1 | 12/2004 | Gruszecki et al. |
| 2005/0245839 A1 | 11/2005 | Stivoric et al. |
| 2005/0276309 A1 | 12/2005 | Koch |
| 2005/0283081 A1 | 12/2005 | Lin et al. |
| 2006/0122473 A1 * | 6/2006 | Kill .................... G01J 5/04 600/300 |
| 2007/0038048 A1 | 2/2007 | Gerder |
| 2007/0038141 A1 | 2/2007 | Koch |
| 2008/0300819 A1 | 12/2008 | Koch |
| 2012/0029310 A1 * | 2/2012 | Paquet ................ A61B 5/0008 600/301 |
| 2012/0065540 A1 | 3/2012 | Yarden et al. |
| 2015/0120249 A1 * | 4/2015 | Hernke ................ A61B 5/0205 702/189 |

* cited by examiner

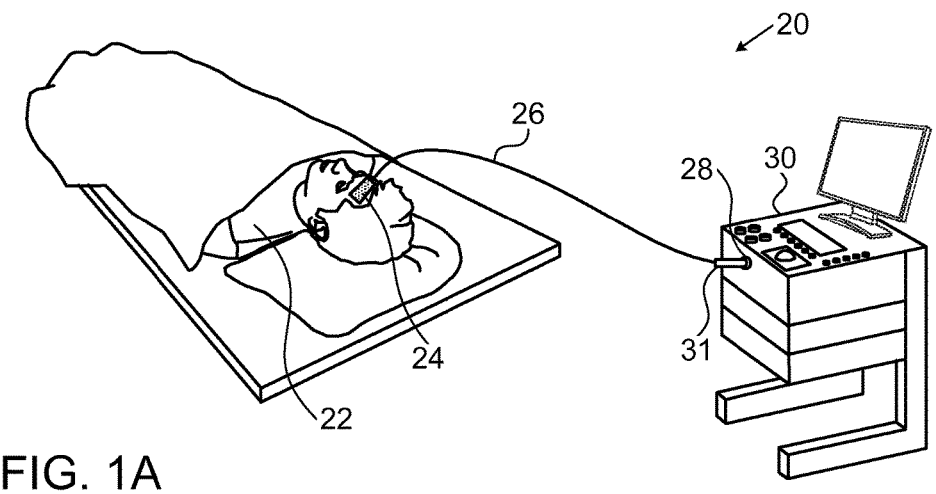
FIG. 1A
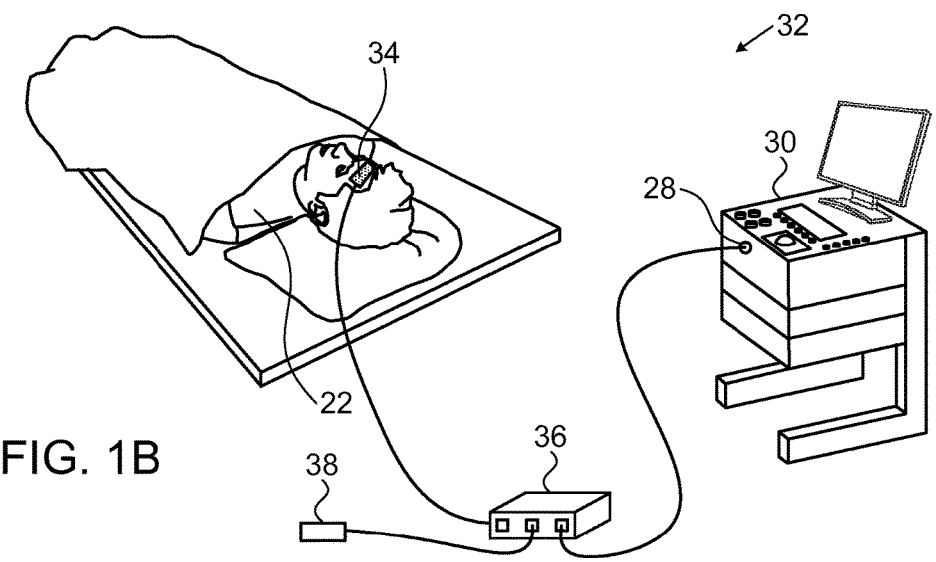
FIG. 1B
FIG. 2
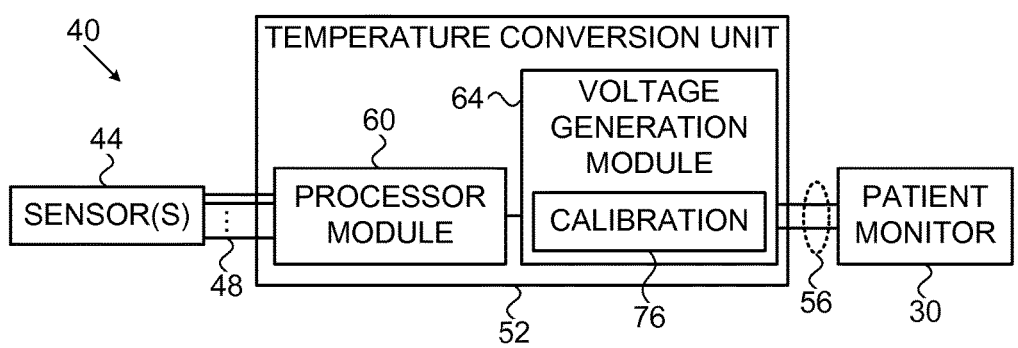

INTERFACE BETWEEN VITAL-SIGNS SENSORS AND PATIENT MONITOR

FIELD OF THE INVENTION

The present invention relates generally to monitoring of vital signs, and particularly to methods and systems for interfacing between vital-sign sensors and patient monitors.

BACKGROUND OF THE INVENTION

Monitoring of patient vital signs is used in various medical environments, such as hospital wards, operating rooms and Intensive Care Units (ICUs). Vital-signs monitors, also referred to as Patient Monitors (PMs), typically monitor physiological parameters such as temperature, heart rate and peripheral oxygen saturation ($S_pO_2$) in the blood, among others.

Many vital-signs monitors include a standard plug for connecting to a thermistor-based temperature probe. Probes of this type were originally developed and standardized by YSI Inc. and include the YSI 400 and YSI 700 types. Such probes include a thermistor sensor, with a calibrated temperature response, and a cable with a standard connector for plugging into the monitor. The vital-signs monitor simply measures the resistance value across the output connector of the cable. The monitor calculates and displays the temperature according to the measured resistance and the known calibration curve.

Patient temperature measurement can be performed using various kinds of temperature sensors. Some types of temperature sensors are non-invasive, and typically measure the body-surface temperature. Non-invasive temperature sensors are described, for example, in U.S. Pat. No. 7,625,117 and in U.S. Patent Application Publication 2009/0299682, whose disclosures are incorporated herein by reference.

U.S. Pat. No. 7,641,390, whose disclosure is incorporated herein by reference, describes a method for digitally controlling the resistive output of a temperature probe. The method uses a temperature sensor, a processor and means under the control of the processor for modifying the resistive output, such as a digital potentiometer. In one embodiment, the processor reads the temperature sensor and adjusts the potentiometer based on a correlative or predictive technique so as to provide a modified output that matches that of a standard resistive temperature probe and is compatible for display on a multi-parameter monitor.

U.S. Pat. No. 7,484,887, whose disclosure is incorporated herein by reference, describes an interface for a monitor and a temperature probe including a temperature sensor. The interface includes a logic circuit for determining a modified resistive output for the temperature sensor and a means for providing the modified resistive output. The means for providing the modified resistive output includes a Field-Effect Transistor (FET), which is coupled to the logic circuit via a first terminal and via a feedback arrangement, providing a FET resistance corresponding to the modified resistive output.

U.S. Patent Application Publication 2012/0065540, whose disclosure is incorporated herein by reference, describes a temperature sensor with calibrated analog resistive output. In some embodiments, a thermometric apparatus includes at least one body-surface sensor, which is configured to be placed at a location on a body surface of a patient and generates a sensor output that varies according to a body-surface temperature at the location. Analog conversion circuitry is coupled between the at least one body-surface sensor and a connector for coupling to a patient monitor. The circuitry is configured to convert the sensor output into an output resistance across the connector that is indicative of a corrected temperature of the patient.

SUMMARY OF THE INVENTION

An embodiment of the present invention that is described herein provides an apparatus including at least one sensor, a connector and a conversion unit. The at least one sensor is configured to be coupled to a body of a patient so as to measure a physiological parameter of the body. The connector is configured for coupling to a patient monitor, which measures a value of the physiological parameter by applying a test signal via the connector and measuring a response signal on the connector in response to the test signal. The conversion unit is coupled between the at least one sensor and the connector, and is configured to determine a corrected value of the physiological parameter, to calculate an auxiliary signal that, in combination with the test signal produced by the patient monitor, causes the response signal on the connector to represent the corrected value of the physiological parameter, and to generate and output the auxiliary signal to the connector so as to cause the patient monitor to measure the corrected value.

In some embodiments, the physiological parameter includes a temperature of the body. In an example embodiment, the at least one sensor includes a body-surface temperature sensor, the measured value includes a body-surface temperature, and the corrected value includes an estimated inner-body temperature. In an embodiment, the measured value includes interim temperature measurements, and the corrected value includes a predicted equilibrium temperature calculated based on the interim temperature measurements. In some embodiments, the conversion unit is configured to read a resistance of the at least one sensor, and to calculate the auxiliary signal based on the resistance.

In an embodiment, the test signal includes a known current that the patient monitor causes to flow through the at least one sensor, the response signal includes a desired voltage across the connector, and the conversion unit is configured to calculate the auxiliary signal that would produce the desired voltage across the connector in response to the known current. In another embodiment, the test signal includes a known voltage that the patient monitor applies across the connector, the response signal includes a desired current flowing through the connector, and the conversion unit is configured to calculate the auxiliary signal that would produce the desired current through the connector in response to the known voltage.

In some embodiments, the conversion unit is configured to calibrate a relation between the test signal and the response signal on the connector, and to generate the auxiliary signal based on the calibrated relation. In a disclosed embodiment, the conversion unit is configured to calibrate the relation by connecting multiple known resistances to the connector, and measuring respective response signals or test signals corresponding to the respective known resistances. The conversion unit may be configured to connect the multiple known resistances, for example, using two or more selectable resistors or a digital potentiometer. In another embodiment, the conversion unit is configured to generate the auxiliary signal using a Pulse-Width Modulation (PWM) circuit. In yet another embodiment, the conversion unit is configured to generate the auxiliary signal using a Digital to Analog Converter (DAC).

There is additionally provided, in accordance with an embodiment of the present invention, a method including coupling to a body of a patient at least one sensor, which measures a physiological parameter of the body, for output by a patient monitor that measures a value of the physiological parameter by applying a test signal via the connector and measuring a response signal on the connector in response to the test signal. A corrected value of the physiological parameter is determined. An auxiliary signal that, in combination with the test signal produced by the patient monitor, causes the response signal on the connector to represent the corrected value of the physiological parameter, is calculated. The auxiliary signal is generated and output to the connector, so as to cause the patient monitor to measure the corrected value.

The present invention will be more fully understood from the following detailed description of the embodiments thereof, taken together with the drawings in which:

BRIEF DESCRIPTION OF THE DRAWINGS

FIGS. 1A and 1B are schematic, pictorial illustrations of systems for patient monitoring, in accordance with embodiments of the present invention;

FIG. 2 is a block diagram that schematically illustrates a system for patient monitoring, in accordance with an embodiment of the present invention;

DETAILED DESCRIPTION OF EMBODIMENTS

Overview

Figure 3:
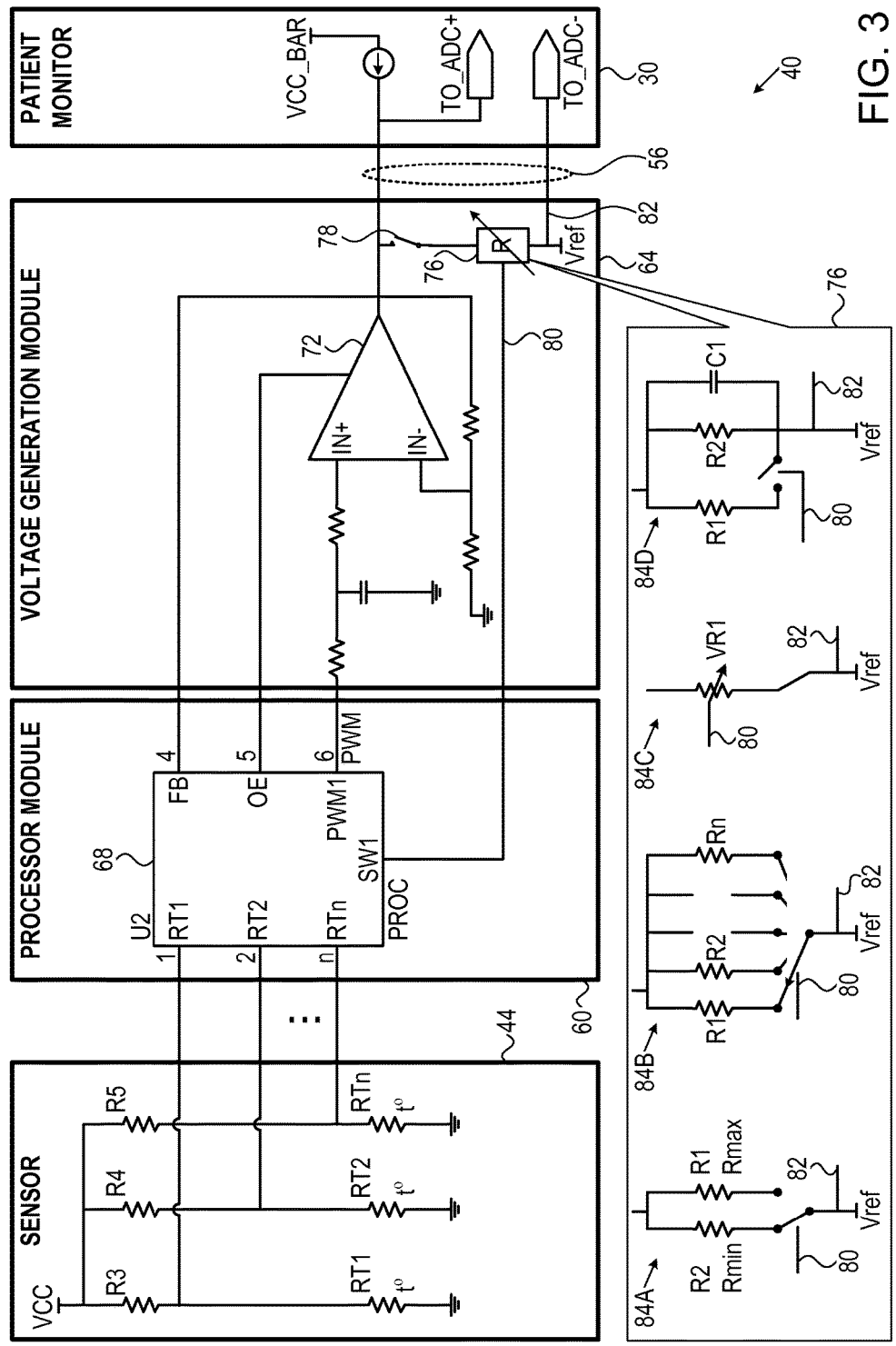
FIG. 3 is a circuit diagram of elements of a system for patient monitoring, in accordance with an embodiment of the present invention.

Embodiments of the present invention that are described herein provide improved methods and systems for measuring and monitoring patient physiological parameters. The embodiments described herein focus on temperature monitoring, although the disclosed techniques can be used, mutatis mutandis, in monitoring various other types of physiological parameters.

A typical patient monitoring system comprises a temperature sensor and a Patient Monitor (PM). The temperature sensor typically comprises a thermistor that changes its resistance depending on the measured temperature. The PM measures the resistance across its input connector, and displays the corresponding temperature value. Typically, the temperature-resistance dependence of the sensor is known, and the PM uses this dependence to translate the measured resistance to temperature.

In practice, however, it is sometimes useful for the PM to display a corrected temperature that differs from the temperature measured by the sensor. For example, in some scenarios the sensor measures the body-surface temperature, but the PM should display an estimate of the core-body temperature or some other inner-body temperature. As another example, it is sometimes desirable to measure temperature over a short time period, and use these measurements to predict and display the equilibrium temperature (which typically stabilizes only after several minutes). Another use-case for displaying a corrected temperature is when the temperature sensor uses a resistance-temperature dependence that is different from the dependence known to the PM. In yet another scenario, the temperature sensor is not a resistive-type sensor, but has a voltage output rather than resistive output, such as in an Infra-Red (IR) or thermocouple sensor. In all the above cases, the output of the temperature sensor should be modified or converted in order to display the desired temperature on the PM.

In some disclosed embodiments of the present invention, a temperature conversion unit is connected between the temperature sensor and the input connector of the PM. The temperature conversion unit carries out a conversion that causes the PM to display the corrected temperature instead of the temperature measured by the sensor. Several example conversion schemes and implementations are described herein. The conversion schemes described herein are active, in the sense that they generate and impose on the PM a corrected voltage or current, which causes the PM to display the desired corrected temperature. These techniques are in sharp contrast to passive conversion schemes that merely reflect a modified resistive output to the PM.

Typically, the PM is conventionally designed to measure the resistance across its input connector by applying a test signal to the connector (e.g., known voltage across the connector or known current through the connector), and measuring a resulting response signal on the connector (e.g., the current flowing through the connector in response to the known voltage, or the voltage developing across the connector in response to the known current). This sort of conventional design assumes that the sensor coupled across the connector is a passive, resistive sensor, such as a thermistor. Such PM designs typically assume that the sensor has some known resistance-temperature dependence, such as YSI-400.

In order to cause the PM to display a corrected temperature that is different from the temperature measured by the sensor, the temperature conversion unit generates an auxiliary signal (voltage or current) that, in combination with the test signal produced by the PM, causes the resulting response signal to indicate the corrected temperature instead of the measured temperature. This sort of correction is referred to herein as "active conversion"—as opposed to "passive conversion" that merely provides the PM with a modified resistive output.

In an example embodiment, the PM applies a known voltage across the connector, and deduces the temperature from the current that flows through the connector (and is thus expected to be proportional to the resistance of the sensor). In this embodiment, the temperature conversion unit may calculate and generate an auxiliary voltage that, jointly with the known voltage applied by the PM, causes a current that corresponds to the corrected temperature. Generally, however, the test signal, response signal and auxiliary signal may each comprise either a current or a voltage. The temperature conversion unit may generate the auxiliary signal in any suitable way, such as using a Pulse-Width Modulation (PWM) circuit or a Digital to Analog Converter (DAC).

In some embodiments, although not necessarily, the temperature conversion unit carries out a calibration process that connects various known resistances and records the resulting response signal levels. Using this calibration, the temperature conversion unit is able to calculate the appropriate auxiliary signal, without relying on any a-priori knowledge as to the mode of operation of the PM.

In summary, the disclosed techniques provide highly-accurate temperature conversion between the temperature sensor and the PM. These techniques enable, for example, the use of non-invasive body-surface temperature sensors while still displaying the core-body temperature.

System Description

FIG. 1A is a schematic, pictorial illustration of a patient monitoring system 20, in accordance with an embodiment of the present invention. The system typically monitors multiple physiological parameters of a patient 22 in an operating room or hospital ward. The present example refers mainly to the parts of the system that are involved in temperature measurement. Nevertheless, the disclosed techniques can be used in measurements of other suitable physiological parameters, such as, for example, heart rate, blood perfusion, blood pressure and/or oxygen saturation ($S_pO_2$).

In the example of FIG. 1A, a temperature-sensing patch 24 is affixed to the patient's body surface, such as to the skin of the patient's forehead or elsewhere on the body. Patch 24 comprises one or more temperature sensors, which measure the body-surface temperature, along with some ancillary circuitry (e.g., sensor sampling) and possibly one or more ambient temperature-measurement sensors (not shown explicitly in the figure).

A temperature conversion unit 31 is mounted on or connected to a cable 26 that connects patch 24 with a Patient Monitor (PM) 30. Unit 31 reads the temperature measured by patch 24, and causes PM 30 to display a converted temperature that is computed based on the measured temperature. Example temperature conversion techniques (which can also be used for conversion and display of other physiological parameters) are explained in detail below. In some embodiments, unit 31 further comprises an ambient sensing probe that senses the ambient room temperature.

In the present example, unit 31 is mounted immediately adjacent to a connector plug 28 of cable 26, which plugs into PM 30. For example, unit 31 may be implemented as a dongle. In another example, unit 31 may be mounted at some middle location along cable 26. In yet another example, the interconnection between patch 24 and unit 31, and/or the interconnection between unit 31 and PM 30, may be wireless. The patient monitor typically comprises a processor, with suitable input circuits for receiving signals from various physiological sensors. The input circuits include a standard receptacle for receiving plug 28.

Conventionally, monitor 30 measures the resistance across plug 28 and converts the resistance to a temperature value according to a pre-programmed calibration function. The monitor typically displays the resulting temperature measurement and may also track the value over time and issue alarms when the temperature moves outside a preset safety range. Although the description that follows refers mainly to visual display of temperature, in alternative embodiments the patient monitor may output the temperature, to an operator or to another system, in any other suitable way. Recording the temperature for subsequent analysis is also regarded herein as a form of output.

FIG. 1B is a schematic, pictorial illustration of a patient monitoring system 32, in accordance with another embodiment of the present invention. The principles of operation of system 32 are similar to those of system 20, as described above. In system 32 a temperature-sensing patch 34 on the patient's body measures the body-surface temperature (or temperatures) and possibly other vital signs. A temperature conversion unit 36 is contained in a separate enclosure and is connected by a cable to patch 34. An ambient sensing probe 38 contains one or more ambient-temperature measurement sensors, such as thermistors. Patch 34 and probe 38 are connected via cables to circuitry 36. Alternatively, ambient sensing probe 38 may be mounted on the enclosure of circuitry 36. Typically, circuitry 36 is powered by a suitable power source (now shown in the figures). The power source may comprise, for example, a battery, a power supply, or both.

In other embodiments, not shown in the figures, alternative system configurations may be used. In an example implementation, the system comprises one processor (referred to as a sampling processor) located on the patch and another processor (referred to as a conversion processor) located in the temperature conversion unit. The two processors may be connected by a wire or wireless link. The sampling processor samples the temperature sensor output and generates digital signals that are transmitted to the conversion processor. This implementation is highly effective against noise and interference, which are common in medical environments. In a specific example the temperature-sensing patch may be connected to a wireless transmitter via a short (e.g., 40 cm) cable to avoid cross contamination. In this configuration, the patch may be disposable while the transmitter may be re-usable.

In yet another embodiment, temperature conversion unit 36 may be integrated with patch 34. Alternatively, one or more ambient-measurement thermistors may be integrated with patch 34, thus obviating probe 38, while circuitry 36 is housed in a separate unit. Further alternatively, any other suitable configuration can be used.

Example Use-Cases

The techniques described herein can be used in a wide variety of scenarios and use cases, in which it is useful or necessary for the PM to display a temperature that differs from the temperature measured by the temperature sensor.

For example, in some scenarios the sensor measures the body-surface temperature, but the PM should display an estimate of some inner body temperature, such as the core-body temperature (defined as the temperature at the pulmonary artery), oral temperature, rectal temperature, axillary temperature, esophageal temperature, or any other suitable inner body temperature.

In another example scenario, it is sometimes desirable to operate in a predictive mode, i.e., to measure temperature over a short time period and use these measurements to predict the long-term equilibrium temperature measurement. Typically, temperature measurement stabilizes and reaches equilibrium after six to ten minutes. It is often desirable to shorten the measurement time to a time period of, for example, 10-120 seconds, so as to make the procedure easier both for the patient and for the care-giver.

Another use-case is when the temperature sensor has a resistance-temperature dependence that is different from the dependence known to the PM, or when the sensor is not a resistive-type sensor but has a voltage input rather than resistive output.

In all of these cases, as well as others, embodiments of the present invention can be used for converting the temperature measured by the temperature sensor or sensors, and causing the PM to display the corrected temperature.

Active Temperature Conversion Schemes

Typically, PM 30 monitors temperature by measuring the resistance across connector 28, and translating the measured resistance into a temperature value to be displayed. The PM typically measures the resistance indirectly, e.g., by measuring the voltage across its input connector for a known applied current, or based on a known voltage applied across an internal resistor. The translation typically follows a known calibrated temperature-resistance curve that characterizes the temperature sensor (or using a temperature-voltage curve that takes into account the temperature-resistance dependence as well as the voltage-current dependence applied by the monitor). Temperature-resistance curves of this sort are specified, for example, in de-facto standards such as YSI 400 and YSI 700.

In some PM implementations, the PM applies a known voltage across connector 28, and measures the current that flows through the connector in response to the known voltage. This sort of measurement may be implemented, for example, using a voltage divider, a Wheatstone bridge, or any other suitable scheme. In other PM implementations, the PM causes known current to flow through connector 28, and measures the voltage across the connector in response to the known current. These configurations are also referred to as "current source" configurations. In both cases, the PM calculates the resistance across connector 28 from the measurement using Ohm's law or the equivalent voltage as explained above. The calculation usually takes into account the PM's internal resistance.

Generalizing the above examples, PM 30 applies a certain test signal (e.g., known voltage or current) to connector 28, and measures the resulting response signal (e.g., resulting current or voltage) on the connector. The measured response signal can then be translated to resistance and then to temperature, using the known resistance-temperature curve. Alternatively, the measured response signal may be translated directly to temperature, e.g., using a look-up table, a predetermined formula embedded in the PM, or any other suitable means.

As noted above, the temperature conversion unit causes PM 30 to display a corrected temperature instead of the temperature measured by the temperature sensor. For this purpose, the temperature conversion unit generates an auxiliary signal (voltage or current) that, in combination with the test signal produced by the PM, causes the resulting response signal to indicate the corrected temperature instead of the temperature measured by the sensor.

In embodiments in which the PM applies a known voltage across the connector, the temperature conversion unit generates an auxiliary voltage that, jointly with the known voltage applied by the PM, causes the current through the connector to correspond to the corrected temperature. In embodiments in which the PM causes known current to flow through the connector, the temperature conversion unit generates an auxiliary current or voltage that, jointly with the known current applied by the PM, causes the voltage across the connector to correspond to the corrected temperature.

Generally, the test signal, response signal and auxiliary signal may each comprise either a current or a voltage. In some embodiments that are described further below, the temperature conversion unit is compatible with any suitable type of PM, without making prior assumptions as to the PM's mode of operation (known voltage or known current). In the disclosed embodiments, the impedance of the PM is typically matched to the impedance of the temperature conversion unit seen by the PM.

FIG. 2 is a block diagram that schematically illustrates a system 40 for patient monitoring, in accordance with an embodiment of the present invention. System 40 may be implemented in the configuration of FIG. 1A, in the configuration of FIG. 1B, or in any other suitable configuration.

System 40 comprises one or more temperature sensors 44, e.g., non-invasive body-surface temperature sensors. Each sensor 44 typically comprises a thermistor that changes its resistance as a function of temperature. (As noted above, in some embodiments system 40 comprises a sampling processor that is adjacent to sensors 44, and a conversion processor in unit 52. In other words, the functions of processor module 60 may be split between the sampling processor and the conversion processor.

System 40 comprises a temperature conversion unit 52, which is connected between sensors 44 and PM 30. Unit 52 is connected to sensors 44 using lines 48 (which may also comprise a wireless link), and to PM 30 using a connector 56. Unit 52 can be used for implementing unit of FIG. 1A or unit 36 of FIG. 1B, for example. Temperature conversion unit 52 comprises a processor module 60 and a voltage generation module 64. Voltage generation module 64 comprises a calibration unit 76, which carries out an automatic calibration process that is described in detail below. An example circuit implementation of modules 60 and 64 is given in FIG. 3 below.

The functional division of functions between modules 60 and 64 is presented purely by way of example. In alternative embodiments, the temperature conversion unit may be implemented using any other suitable internal configuration. In an example embodiment, processor module 60 controls the automatic calibration process carried out by unit 76, which learns the PM characteristics (e.g., internal resistance), as will be described further below. In one embodiment, processor module 60 reads the resistance of each temperature sensor 44, which corresponds to the temperature measured by that sensor. Module 60 calculates the corrected temperature that should be displayed by PM 30 in accordance with the measured temperature and the ambient temperature.

Module 60 may derive the corrected temperature from the measured sensor temperature in any suitable way, such as using a predefined table or function. In an example embodiment, the corrected temperature is given by a linear combination of the measured body temperature and the ambient temperature. Additional details regarding the relation between measured and corrected temperature are addressed, for example, in U.S. Pat. Nos. 6,280,397, 7,479,116, 7,597, 668 and 8,185,341, whose disclosures are incorporated herein by reference, and in U.S. Pat. Nos. 7,484,887 and 7,641,390 and U.S. Patent Application Publication 2012/ 0065540, cited above.

Voltage generation module 64 generates an auxiliary signal that, in combination with the test signal generated by PM 30, causes the response signal on connector 56 to correspond to the corrected temperature calculated by processing module 60. The voltage generation module applies this auxiliary signal (voltage or current) to connector 56. As a result, PM 30 is forced to display the corrected temperature instead of the temperature measured by the sensor.

In alternative embodiments, the functionality of processor module 60 is split between two processors—A sampling processor that is located adjacent to sensors 44, and a conversion processor that is adjacent to module 64. The sampling processor and the conversion processor may be linked using any suitable interface, for example a wireless link.

Example Circuit Implementation

FIG. 3 is a circuit diagram of elements of system 40, in accordance with an embodiment of the present invention. In this example, the system comprises three temperature sensors 44, comprising n respective thermistors denoted RT1 . . . RTn.

Processor module 60 comprises a processor 68, which reads the resistances of the n thermistors and calculates the corresponding desired corrected temperature to be displayed on the PM and the appropriate auxiliary signals (voltages or currents) that should be applied in order for PM 30 to display the desired corrected temperature. Voltage generation module 64 comprises at least one operational amplifier 72, which is connected in a feedback configuration.

At a given time, the output of amplifier 72 produces a given auxiliary signal, which is then applied to connector 56 of PM 30. This auxiliary signal, together with the internal test signal of the PM (current or voltage—marked with a current source in the figure), causes the PM to display the appropriate corrected temperature.

In the embodiment of FIG. 3, processor 68 controls amplifier 72 to produce the desired auxiliary signal using Pulse-Width Modulation (PWM). In this implementation, pin #6 of processor 68 produces a square-wave PWM signal that alternates between two voltage levels with a controlled duty-cycle. Processor 68 adjusts the duty cycle of the PWM signal such that the average voltage is proportional to the desired auxiliary signal. The PWM signal is filtered by a resistor-capacitor T-network, and then provided as input to amplifier 72. In response to the PWM signal at its input, amplifier 72 generates the desired auxiliary signal at its output.

In an alternative embodiment, processor 68 uses a Digital-to-Analog Converter (not shown in the figure) instead of a PWM circuit to control voltage generation module 64. In this embodiment, the processor controls the DAC to generate a control signal that is proportional to the desired auxiliary signal. The DAC output (voltage or current) is provided as input to operational amplifier 72. Further alternatively, processor 68 may control voltage generation module 64 to generate the desired auxiliary signals in any other suitable way.

Automatic Calibration Scheme

In some embodiments, temperature conversion unit 52 does not make any a-priori assumptions as to the mode of operation of PM 30. In these embodiments, unit 52 carries out an automatic calibration process that learns the PM characteristics (e.g., internal resistance and signals). Using the calibration results, unit 52 is able to accurately set the auxiliary signals, regardless of whether the PM uses voltage-source or current-source measurement and regardless of the actual internal resistance of the PM.

In an example embodiment (illustrated in FIG. 3) voltage generation module 64 comprises a calibration unit 76, which comprises a configurable resistance element. Unit 76 can be set by processor 68 to two or more known resistances, which are applied across connector 56 during calibration. Typically, these known resistances are chosen to be properly representative of the full range of minimal to maximal measured temperatures-resistances by the PM. Typically, the output of amplifier 72 is disabled during this process, so that the only resistance across connector 56 is that of unit 76. By alternating between different resistances of unit 76, processor 68 is able to measure the actual voltages that develop across connector 56 in response to various resistances. Unit 76 is typically connected across connector 56 of the PM only during calibration. During normal operation, unit 76 is disconnected, e.g., using a switch 78.

In some embodiments, system 40 comprises measurement circuitry that measures the voltage across (or current through) the known resistance connected to the PM. In the example of FIG. 3, the voltage across connector 56 is fed back to a feedback (FB) pin of processor 68 (pin 4, denoted FB). Processor 68 digitizes the voltage on its FB pin using an internal Analog-to-Digital Converter (ADC). Alternatively, any other suitable measurement circuitry can be used.

In a typical calibration process, processor 68 sets various arbitrary resistances within the resistance range expected by the PM in unit 76, measures the resulting voltages (response signals) on connector 56, and builds a Look-Up Table (LUT) that translates between the measured response signals and resistance. During normal operation, processor 68 calculates the corrected temperature to be displayed by the PM (based on the measured sensor temperature and some correction algorithm), and then uses the known resistance-temperature dependence such as YSI 400 to determine the resistance that is expected by the PM in order to display the corrected temperature. Based on the desired resistance and the LUT, processor 68 calculates the auxiliary signal that corresponds to the desired resistance. Processor 68 then causes module 64 to generate the auxiliary signal that corresponds to this resistance.

In another example calibration process, the LUT translates temperatures directly into voltages. In this process, processor 68 sets various arbitrary resistances within the resistance range expected by the PM in unit 76, and measures the resulting voltages (response signals) on connector 56. Using a known temperature-resistance dependence such as YSI 400, processor 68 builds a LUT that translates between the measured response signals and respective temperatures to be displayed on the PM. During normal operation, processor calculates the corrected temperature to be displayed by the PM (based on the measured sensor temperature and some correction algorithm). Based on the corrected temperature and the LUT, processor 68 calculates the auxiliary signal that corresponds to the corrected temperature. Processor 68 then causes module 64 to generate the auxiliary signal that corresponds to this resistance.

In another embodiment, processor 68 builds a database, which comprises the internal resistance and the voltage that PM 30 applies. Based on this data, the processor module is able to calculate the auxiliary voltage needed in order to emulate the resistance corresponding to the desired displayed temperature. Example calibration schemes and formulas for constructing such a database are provided further below.

Unit 76 may be implemented in various ways. Four examples are shown at the bottom of FIG. 3. In all these examples, processor 68 sets the resistance of unit 76 using a control signal 80. A reference voltage $V_{ref}$ is applied to one terminal of unit 76 (denoted 82), which is also connected to one terminal of connector 56. The other terminal of unit 76 is connected to the second terminal of connector 56.

In a first example (denoted 84A), unit 76 comprises two resistors R1 and R2, which are selected by signal 80. Typically, resistors R1 and R2 are set to the maximum and minimum resistances ($R_{max}$ and $R_{min}$) of the resistance range of interest. When using YSI 400 temperature sensors, for example, R1 and R2 may be on the order of 2KΩ and 1KΩ, respectively. This example enables relatively coarse calibration using two data points.

In a second example (denoted 84B), unit 76 comprises n resistors R1 . . . Rn, which are selected by signal 80. The resistances of resistors R1 . . . Rn are typically distributed across the resistance range of interest, e.g., 1KΩ to 2KΩ.

This implementation enables higher-accuracy calibration using multiple data points. A third implementation example (denoted 84C) enables even finer calibration. In this example, unit 76 comprises a digital potentiometer (denoted VR1) that is controlled by signal 80.

In a fourth implementation example (denoted 84D), control signal 80 is a PWM signal that toggles the switch so as to alternate between resistances R1 and R2 at a certain duty cycle. By controlling the PWM duty cycle, control signal 80 is able to create various effective resistances.

Let D and Fpwm denote the duty cycle and frequency of signal 80, respectively, such that D=0 means a constantly-open switch and D=1 means a constantly-closed switch. The effective resistance of unit 76 is Reff=Rp·D+R1(1−D), wherein Rp=R1·R2/(R1+R2). Varying the duty cycle enables setting of effective resistances in the range Rp≤Reff≤R1. For smooth circuit operation, capacitance C1 should typically be chosen such that Reff·C1>>1/Fpwm. Further alternatively, calibration unit 76 may be implemented in any other suitable way.

The system configurations shown in FIGS. 1A, 1B and 2, and the temperature conversion unit configuration shown in FIG. 3, are example configurations that are chosen purely for the sake of conceptual clarity. In alternative embodiments, any other suitable configuration can be used. Some elements of the patient monitoring system, and in particular the temperature conversion unit, may be implemented in hardware, e.g., in one or more Application-Specific Integrated Circuits (ASICs) or Field-Programmable Gate Arrays (FPGAs). Additionally or alternatively, some elements of the system, including elements of the temperature conversion unit, can be implemented using software, or using a combination of hardware and software elements.

Some of the system functions, such as the functions of processor module 60, may be carried out using a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

Example Patient Monitor Models and Associated Calibration Schemes

In various embodiments, processor 68 of temperature conversion unit 52 performs the above-described automatic calibration under some assumption as to the structure of PM 30. Two example types of PMs are a voltage-divider-based PM and a Wheatstone-bridge-based PM. In other embodiments, processor 68 does not make any such assumptions and regards the PM as a "black box."

Figure 4A:
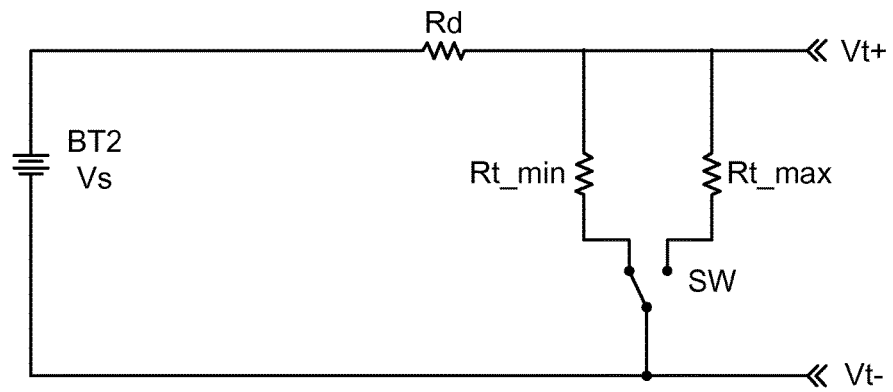
FIGS. 4A and 4B are electrical models of Patient Monitors (PM), used for calibration of a system for patient monitoring, in accordance with embodiments of the present invention.

FIG. 4A is an electrical model of a voltage-divider-based PM, which is used for calibration of temperature conversion unit 52, in accordance with an embodiment of the present invention. In this model, Vs denotes the internal voltage applied by the PM, Rd denotes the internal serial resistance of the PM, Rt_min denotes the minimal expected resistance of the temperature sensor, Rt_max denotes the maximal expected resistance of the temperature sensor, and Vt denotes the voltage drop across the temperature sensor (i.e., across connector 56).

The temperature-dependent resistance of the temperature sensor is denoted Rt. In an embodiment, Rt_min and Rt_max are chosen as the minimal and maximal resistances in the YSI400 range of interest, respectively. The assumption in this model is that, in order to measure temperature, the PM measures Vt, which is a function of Rt. The relationship between Vt and Rt is given by:

$$Vt = Vs \frac{Rt}{Rd + Rt}$$

and therefore:

$$Rt = \frac{Rd}{\frac{Vs}{Vt} - 1}$$

The PM is assumed to measure Vt and use the above relationship to derive Rt and thus the temperature. Therefore, knowledge of Rd and Vs of the PM enables unit 52 to calculate the desired voltage Vt that needs to be applied across connector 56 in order to cause the PM to measure any desired temperature.

In an example process for estimating Rd and Vs of the PM, unit 52 connects two resistances Rt_min and Rt_max to connector 56, one resistance at a time. By measuring the voltage drop across connector 56 in the presence of each resistance, unit 52 is able to derive Rd and Vs.

Analysis of the circuit of FIG. 4A gives the following relationships:

$$I\text{min} = \frac{Vt\text{min}}{Rt\text{min}}$$

$$I\text{max} = \frac{Vt\text{max}}{Rt\text{max}}$$

Let Vd_min and Vd_max denote the minimal and maximal voltages across the constant resistance Rd, we get:

$Vs = Vd\_\text{min} + Vt\_\text{min}$ $Vs = Vd\_\text{max} + Vt\_\text{max}$

By subtracting the two equations, and assuming the same currents Imin and Imax flow through Rd, we get:

$Vt\text{max} - Vt\text{min} = Rd(I\text{min} - I\text{max})$ or $$Rd = \frac{Vt\text{max} - Vt\text{min}}{I\text{min} - I\text{max}}$$

and therefore:

$Vs = Rd \cdot I\text{max} + Vt\text{max}$ or $Vs = Rd \cdot I\text{min} + Vt\text{min}$ By using the voltage-divider relationship, we get:

$$Vtx = \frac{Vs}{\left(\frac{Rd}{Rx} + 1\right)}$$

wherein Rx denotes any desired sensor resistance, and Vtx denotes the value of Vt needed to cause the PM to measure resistance Rx (and thus the corresponding temperature). The equation above gives the translation between voltage and resistance, but knowing the temperature-resistance dependence, this translation is equivalent to a direct translation between voltage and temperature.

Figure 4B:
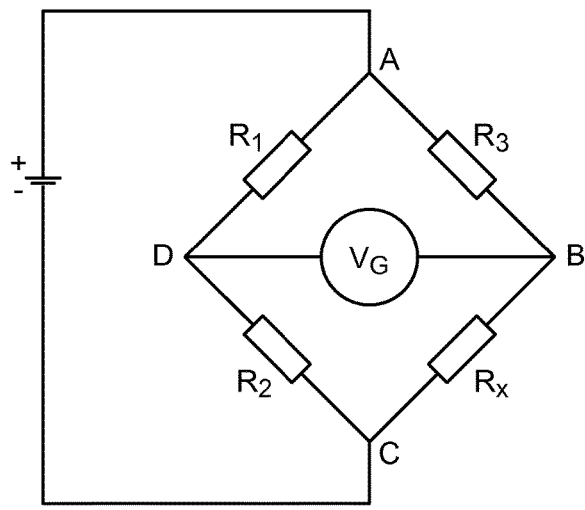

FIG. 4B is an electrical model of a Wheatstone-bridge-based PM, which is used for calibration of temperature conversion unit 52, in accordance with another embodiment of the present invention. In such a PM, the relationship between the temperature-dependent resistance Rx and the voltage Vg (measured between points B and D in the figure) is given by:

$$Vg = \left(\frac{Rx}{R3+Rx} - \frac{R2}{R1+R2}\right) Vs$$

or $$Vg = Vs\frac{Rx}{R3+Rx} - Vs\frac{R2}{R1+R2}$$

The equation above can be written as $$Vg = Vt - V0$$

wherein V0 is a constant voltage of the R1-R2 voltage divider. This equation means that, for a Wheatstone-bridge PM, a similar calibration procedure can be used as used above for voltage-divider PMs.

In other embodiments, unit 52 may assume that the temperature-voltage dependence in the PM (e.g., for a voltage divider between internal resistance Rd and temperature-dependent resistance Rt) is close to linear. Therefore, unit 52 may use linear interpolation to calculate Vt as a function of the desired temperature T. For example, unit 52 may measure Vt_min and Vt_max for two constant resistors Rt_min and Rt_max, which are connected in turn to connector 56 of PM 30. Knowing Tmin and Tmax from YSI400 T-R table, it is possible to calculate any Vt by:

$$Vt = Vt\max - \frac{(T - T\min)(Vt\max - Vt\min)}{T\max - T\min}$$

The above example refers to two data points. Alternatively, the calibration process may be performed using a larger number of data points, so as to improve the calibration accuracy.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus for correcting a measured value from a sensor coupled to a patient, comprising:
   at least one sensor, which is configured to be coupled to a body of the patient so as to measure a physiological parameter of the body;
   a patient monitor having a two leads connector for measuring the physiological parameter by applying an internal monitor voltage or an internal monitor current through the patient monitor's connector to the sensor;
   an active conversion unit, which is coupled between the at least one sensor and the patient monitor connector;
   the active conversion unit is configured to determine at least the internal monitor voltage or the internal monitor current by connecting at least one known resistance, and measuring corresponding voltage or current across the two lead connector;
   the active conversion unit further determines a new auxiliary signal based on the determined internal monitor voltage or the internal monitor current, and determines a corrected value; and
   wherein, the active conversion unit applies the new auxiliary signal to the patient monitor through the two lead connector, the active conversion unit actively causes the patient monitor to display the corrected value of the physiological parameter instead of displaying the measured value of the physiological parameter measured by the at least one sensor.

2. The apparatus according to claim 1, wherein the physiological parameter comprises a temperature of the body.

3. The apparatus according to claim 2, wherein the at least one sensor comprises a body-surface temperature sensor, the measured value comprises a body-surface temperature, and the corrected value comprises an estimated inner-body temperature.

4. The apparatus according to claim 2, wherein the measured value comprises interim temperature measurements, and the corrected value comprises a predicted equilibrium temperature calculated based on the interim temperature measurements.

5. The apparatus according to claim 1, wherein the active conversion unit is configured to read a resistance of the at least one sensor, and to calculate the new auxiliary signal based on the resistance.

6. The apparatus according to claim 1, wherein the active conversion unit is configured to calculate the new auxiliary signal that would produce a voltage in response to a known current or determined current of the patient monitor.

7. The apparatus according to claim 1, wherein the active conversion unit is configured to calculate the new auxiliary signal that would produce a current in response to the known voltage or the determined voltage of the patient monitor.

8. The apparatus according to claim 1, wherein the active conversion unit is configured to connect the multiple known resistances using two or more selectable resistors or a digital potentiometer.

9. The apparatus according to claim 1, wherein the active conversion unit is configured to generate the new auxiliary signal that is voltage or current and jointly with voltage or current applied by the patient monitor causes voltage or current that corresponds to the corrected value displayed on the patient monitor, and wherein the corrected value is a corrected temperature.

10. The apparatus according to claim 1, wherein the active conversion unit is configured to generate the new auxiliary signal using a Digital to Analog Converter (DAC).

11. A method for correcting a measured value from a sensor on a patient, comprising:

applying an internal monitor voltage or an internal monitor current through a patient monitor's two leads connector to at least one sensor;

calibrating a relation between a test signal and a response signal both from the patient monitor, wherein calibrating the relation comprises connecting multiple known resistances, and measuring respective response signals or test signals corresponding to the respective known resistances;

receiving a measurement of a physiological parameter of the patient from the at least one sensor that measures a measured value of the physiological parameter;

determining digitally through an active conversion unit a corrected value of the measured value;

calculating a new auxiliary signal that is produced by the active conversion unit; and generating the new auxiliary signal based on the calibrated relation and applying the new auxiliary signal to a patient monitor through the patient monitor's two lead connector, the active conversion unit actively causing the patient monitor to display the corrected value of the physical parameter instead of the measured value of the physiological parameter measured by the at least one sensor.

12. The method according to claim 11, wherein the physiological parameter comprises a temperature of the body.

13. The method according to claim 12, wherein the at least one sensor comprises a body-surface temperature sensor, the measured value comprises a body-surface temperature, and the corrected value comprises an estimated inner-body temperature.

14. The method according to claim 12, wherein the measured value comprises an interim temperature measurement, and the corrected value comprises a predicted equilibrium temperature calculated based on the interim temperature measurement.

15. The method according to claim 11, wherein calculating the new auxiliary signal comprises reading a resistance of the at least one sensor and calculating the new auxiliary signal based on the resistance.

16. The method according to claim 11, wherein calculating the new auxiliary signal comprises computing the new auxiliary signal that would produce a voltage in response to current or voltage of the patient monitor.

17. The method according to claim 11, wherein calculating the new auxiliary signal comprises computing the new auxiliary signal that would produce a current in response to current or voltage of the patient monitor.

18. The method according to claim 11, wherein connecting the multiple known resistances comprises selecting between two or more selectable resistors or setting a digital potentiometer.

19. The method according to claim 11, wherein generating the new auxiliary signal includes the active conversion unit being configured to generate the new auxiliary signal that is voltage or current and jointly with voltage or current applied by the patient monitor causes voltage or current that corresponds to the corrected value displayed on the patient monitor, and wherein the corrected value is a corrected temperature.

20. The method according to claim 11, wherein generating the auxiliary signal is by using a Digital to Analog Converter (DAC).

* * * * *